United States Patent [19]

Kritzler

[11] Patent Number: 4,692,325
[45] Date of Patent: Sep. 8, 1987

[54] RADIOPAQUE MEDIUM

[75] Inventor: Steven Kritzler, Cronulla, Australia

[73] Assignee: Field Group Chemicals Pty. Ltd., New South Wales, Australia

[21] Appl. No.: 697,338

[22] Filed: Feb. 1, 1985

[63] Continuation of PCT AU 84/00101, filed Jun. 5, 1984, published as WO 84/04888 on Dec. 20, 1984.

[30] Foreign Application Priority Data

Jun. 9, 1983 [AU] Australia ............................. PF9771

[51] Int. Cl.$^4$ .............................................. A61K 37/26
[52] U.S. Cl. ........................................................ 424/4
[58] Field of Search ............................................. 424/4

[56] References Cited

U.S. PATENT DOCUMENTS 3,784,461 1/1974 Fischler .................................. 424/4
4,069,306 1/1978 Rothman ................................ 424/4

FOREIGN PATENT DOCUMENTS 2263754 10/1975 France .................................... 424/4

OTHER PUBLICATIONS

Webster's Third World International Dictionary, p. 1873.
J. H. Hunt and J. F. Anderson, "Double Contrast Upper Gastrointestinal Studies", Clinical Radiology, pp. 87–89.
"Radiology Now Starting The Double Contrast Barium Meal", pp. 610–612.

Primary Examiner—Frederick E. Waddell
Attorney, Agent, or Firm—Barnes & Thornburg

[57] ABSTRACT

There is provided a two part medium for use in double contrast radiography. A first part contains a radiopaque substance for example barium sulphate. A second part is radiolucent. The first part contains a reactant for example Carboxy Methyl Cellulose) which reacts with a component of the second part (for example polyvinyl pyrolidone on contact between the parts to form a compound or complex which inhibits migration of the radiopaque substance into the radiolucent part.

2 Claims, No Drawings

RADIOPAQUE MEDIUM

This is a continuation of PCT application No. PCT/AU84/00101 filed June 5, 1984 and claiming the priority date of Australian patent aplication PF9771 dated June 9, 1983.

TECHNICAL FIELD

This invention relates to a radiopaque medium of particular use in the radiographic examination of the small bowel or intestine. That intestine is of relatively small diameter but of substantial length and as a result its radiographic examination has hitherto presented difficulties, especially when a "double contrast" examination is required.

BACKGROUND ART

A double contrast examination is one in which the wall of the bowel is lined with radiopaque material while the lumen is filled with radiolucent material, so enabling the radiologist to more clearly visualise the surface conditions of each wall. A double contrast study differs from a single constrast study in which the bowel is filled with radiopaque media and in which substantially only the bowel silhouette is rendered visible.

Hitherto attempts to achieve a double contrast study have involved infusing a relatively small quantity of radiopaque media into the duodenum for onward transmission into the small bowel immediately followed by the infusion of a large volume of water or aqueous solution intended to flush the radiopaque material through the bowel while distending the bowel. This technique has severe limitations because the radiopaque material rapidly becomes dispersed in the radiolucent aqueous material and thus in practice the only area available for double contrast examination, and then only briefly, is at the downstream front of the moving aqueous component.

With the foregoing in mind, the present invention was devised to provide a better medium for double contrast radiographic study, by enteroclysis, of the small bowel and which overcomes or at least ameliorates the deficiencies of the prior known media.

DISCLOSURE OF THE INVENTION

According to one aspect the invention consists in a two component medium for use in double contrast radiography comprising:

a first part which contains a radiopaque substance,
a second part which is substantially radiolucent,
said first and said second part after contact forming a compound or complex which inhibits migration of the radiopaque substance from the first part to the second part.

The compound or complex formed may result in a matrix of limited solubility which binds the radiopaque substance within the first part. The compound or complex formed may constitute a zone or barrier at the interface of the first and second part which hinders or prevents diffusion or migration of the radiopaque substance into the radiolucent part.

The compound or complex formed at the interface of the two parts may be insoluble or may be a compound or complex which is only slowly soluble in the first and second part and which thus acts as a diffusion barrier. In other embodiments the compound or complex may form a micellular structure or a liquid crystal structure which acts as a barrier to diffusion of the radiopaque substance into the radiolucent part.

In yet other embodiments the compound or complex may form a zone of higher viscosity than the first part and which inhibits migration of the radiopaque substance into the second part.

In a highly preferred embodiment a water soluble polymer in the radiopaque part interacts or reacts with a water soluble or dispersible polymer in the radiolucent part to form a micellular water dispersible macromolecular complex which prevents migration of the radiopaque substance into the radiolucent part.

In practice, the first part and then the second part are infused via a catheter. The formation of a diffusion barrier at the moving interface of the two components in the bowel restricts the radiopaque substance held within the radiopaque part from dispersing into the second infused part as the second part flushes the first infused part through the bowel whilst distending the same. The end result is a distended bowel substantially full of radiolucent media but with the walls coated with a thin layer of radiopaque material trapped adjacent the wall by a barrier comprising for example a water dispersible matrix of limited solubility.

BEST MODE FOR CARRYING OUT THE INVENTION

By way of example, particular embodiments of the invention are described in more detail hereinafter.

A first embodiment according to the invention comprises a two component medium of which the first part has a composition in the weight percentages as follows:

EXAMPLE 1—FIRST PART

| COMPONENT | % W/W |
| --- | --- |
| Water | 55.73 |
| Vee Gum (Smectite Clay) | 0.25 |
| Sodium Carboxy Methyl Cellulose | 0.61 |
| Sodium Citrate | 0.19 |
| Sodium Hexa Meta Phosphate | 0.09 |
| Potassium Sorbate | 0.12 |
| Methyl Para Hydroxy Benzoate | 0.04 |
| Propyl Para Hydroxy Benzoate | 0.02 |
| Peppermint Oil | 0.01 |
| Simethicone Emulsion | 0.08 |
| Barium Sulphate Powder | Balance |

Vee Gum is obtainable from Vanderbuilt Corp. U.S.A.
The Sodium Carboxy Methyl Cellulose has a viscosity of from 10–20 centipoise in 1% solution in water at 25° C.

The second part has a composition in the weight percentages shown as follows:

EXAMPLE 1—SECOND PART

| COMPONENT | % W/W |
| --- | --- |
| Water | 97.79 |
| PVP K 30 (Polyvinyl Pyrrolidone) | 2.15 |
| Methyl Para Hydroxy Benzoate | 0.04 |
| Propyl Para Hydroxy Benzoate | 0.02 |

Both of the above-mentioned components may include N sulphuric acid or 30% potassium hydroxide as needed to adjust the pH to within the range of 6–6.5 inclusive.

The first part includes barium sulphate powder as a radiopaque substance. The second part is radiolucent. When the first and the second part are brought into contact the sodium carboxy methyl cellulose of the first part reacts with the polyvinyl pyrrolidone of the second part to form a water dispersible micellular complex or matrix of limited solubility at the interface of the first and second parts.

Migration of the barium sulphate from the first part into the second part is thereby prevented or at least inhibited.

The sodium hexa meta phosphate and sodium citrate act as a suspending agent for the barium sulphate and assist to buffer the pH of the system. Potassium sorbate, and methyl and propyl para hydroxy benzoates act as a preservative system. Peppermint oil act as a odourant. The use of suspending agents, preservatives, defoamers, flavourings and the like is conventional and other agents may be added or substituted.

The quantity of Carboxy Methyl Cellulose in the composition of Example 1 first part is selected having regard to a viscosity. The viscosity of the first part must be sufficiently low for administration of the first part via a catheter and sufficiently high to maintain suspension of the barium sulphate. The relative quantities of other ingredients is not critical and may be varied to an extent which may readily determined by experiment.

Other water soluble or water dispersible reactants may be substituted for the sodium carboxy methyl cellulose used in the composition of Example I—first part. For example other cellulose polymers such as alkyl hydroxy celluloses, alkyl hydroxy alkyl celluloses and other cellulose esters. Other reactants which may be substituted for the carboxy methyl cellulose are polysacharides, vinyl ether-maleic anhydride co-polymer, polyvinyl alcohol, and copolymers or mixtures of the foregoing.

Advantageously the first part may contain a mixture of the foregoing reactants for example, sodium carboxy methyl cellulose with a minor proportion of vinyl ether-malelic anhydride copolymer. The finely divided barium sulphate may be incorporated therein. For preference the amount of vinyl ether-maleic anhydride co-polymer is less than 3% by weight of the first part.

The second part may have a polyvinyl pyrolidones, or a mixture of polyvinyl pyrolidones of differing molecular weight, for example PVP K 90 with a lesser quantity of PVP K 30 wherein designations K30 and K90 are believed to be indicative of molecular weights of approximately 40,000 and 360,000 respectively. It will be understood that other constituents may be substituted for the polyvinyl pyrolidones depending on the selected co-reactant of the first part.

Thus while carboxy methyl cellulose in the first part reacts with polyvinyl pyrolidone in the second part to give a micellular complex which is sparingly soluble or slowly dispersible, use of vinyl ether-maleic anhydride polymer in the first part with polyvinyl alcohol in the second part forms an insoluble compound or complex. An insoluble compound may also be formed by including for example a carboxy methyl cellulose in the first part and a soluble trivalent foodgrade metallic salt in the second part.

If a drop of water is placed adjacent a drop of a barium sulphate suspension in water on a microscope slide and the drops are brought into contact, the droplets coalesce and the barium sulphate disperses throughout the coalesced liquid within a few minutes.

If a drop taken from a composition according to Example 1—First Part is placed on the slide adjacent a drop taken from a composition according to Example I—Second Part then when the drops are brought into contact the barium sulphate suspension does not disperse into the second part over a period of many hours.

If the first part contains vinyl ether-maleic anhydride and the second contains polyvinyl pyrolidone, then (if no barium sulphate is present to hide the reaction) an insoluble compound is visible at the boundary of the two drops.

It is of course highly preferred to select foodgrade components and preferably to select a combination of co-reactants which produce a water dispersible product.

When put to use about 200 cc for an average adult of the first part composition may be infused initially to be followed promptly by the infusion of about from 1 to 3 liters of the second part, the quantity depending on the disclosed volume of the particular patients small bowel, the second part being infused at as quick a rate as the patent can tolerate.

For preference, but not essentially, both parts also include various pharmaceutically acceptable additives such as flavouring or odourizing agents, suspending agents, preservatives, defoaming agents and emulsifiers.

Radiopaque substances other than barium sulphate may of course be utilized.

As will be apparent to those skilled in the art from the teaching hereof, the composition of the first and second part may be varied considerably without departing from the inventive concept disclosed herein.

The claims defining the invention are as follows:

1. A system for use in double contrast radiography of patient, said system comprising:
   a first part comprising an aqueous medium which contains finely divided barium sulphate,
   a second part which is a liquid adapted for administration separately from the first part and which is substantially radiolucent,
   said first and second parts, after contact, forming a compound or complex at their interface which inhibits migration of the finely divided barium sulphate from the first part to the part.

2. A two component medium for use in double contrast radiography comprising a first part including an aqueous medium which contains finely divided barium sulphate and a first reactant, and a second part which is substantially translucent and contains a second reactant, said first and second reactants on contact forming a compound or complex which inhibits migration of the finely divided barium sulphate into the second part.

* * * * *